United States Patent [19]
Mathus

[11] Patent Number: 5,972,694
[45] Date of Patent: Oct. 26, 1999

[54] MULTI-WELL PLATE

[76] Inventor: Gregory Mathus, 49 Deer Grass La., Concord, Mass. 01742

[21] Appl. No.: 09/005,542

[22] Filed: Jan. 12, 1998

Related U.S. Application Data

[60] Provisional application No. 60/037,678, Feb. 11, 1997.
[51] Int. Cl.$^6$ .................................................. C12M 3/00
[52] U.S. Cl. .......................... 435/288.4; 435/297.5; 435/305.2; 422/102
[58] Field of Search ........................... 435/297.5, 305.2, 435/288.4; 422/102

[56] References Cited

U.S. PATENT DOCUMENTS

| | | | |
|---|---|---|---|
| 4,871,674 | 10/1989 | Matsui et al. | 435/284 |
| 4,948,442 | 8/1990 | Manns | 156/73.1 |
| 5,026,649 | 6/1991 | Lyman et al. | 435/284 |
| 5,141,718 | 8/1992 | Clark | 422/99 |
| 5,215,920 | 6/1993 | Lyman et al. | 435/284 |
| 5,376,273 | 12/1994 | Pacheco et al. | 210/490 |
| 5,462,874 | 10/1995 | Wolf et al. | 435/297.5 |
| 5,466,602 | 11/1995 | Lyman et al. | 435/297.1 |
| 5,468,638 | 11/1995 | Barker et al. | 435/304.1 |

Primary Examiner—David A. Redding
Attorney, Agent, or Firm—Thomas R. Beall

[57] ABSTRACT

The invention relates to an improved multiwell cluster plate. The wells of the plate each have an upper chamber and a lower chamber separated by a microporous membrane. Adjacent to each well is a corresponding access port. The access port is a separate opening in the tip surface of the plate which provides direct access to the lower chamber of the corresponding well, without disturbing the upper chamber or the membrane

43 Claims, 6 Drawing Sheets

MULTI-WELL PLATE

This application claims benefit of provisional application 60/037,678, filed Feb. 11, 1997.

BACKGROUND

This invent ion relates to a multi-well cluster plate for growing cells or tissue cultures in vitro and more particularly comprises a new and improved cell culture plate and well structure that combines a device for supporting tissue cultures in a fluid medium with a structure that allows unfettered access to the portion of the well below the tissue culture.

Advantages of growing tissue in vitro by supporting a microporous membrane as a cell growth substrate in a culture medium have been known. By supporting a microporous membrane in a nutrient rich medium, a cell layer can be attached and grown on the membrane. This cell layer is able to receive nutrients through the microporous membrane from the medium below. The cell layer is separated from the medium by the membrane. A concentration gradient of nutrients develops and feeds the cells through this permeable membrane. This basolateral method of feeding more closely resembles in vivo conditions in which polarized structures such as epithelial cells functionally behave. Creating more natural cellular conditions is an advantage to scientists studying cell transport and other biological activities.

Cell culture inserts have been used to take advantage of the basolateral feeding technique. Cell culture inserts are comprised of a plastic material with a membrane on the bottom surface. The inserts fit into wells of a culture plate, such that the membrane is suspended within a corresponding well. The well itself contains culture medium into which the metr.-rane is immersed. Conventional cell culture inserts and devices are described in U.S. Pat. No. 4,871,674, U.S. Pat. No. 5,026,649, U.S. Pat. No. 5,215,920, U.S. Pat. No. 5,466,602, and U.S. Pat. No. 5,468,638. Many inserts also include an opening in the hanging support structure which enables access to the culture medium below the membrane. This access is crucial for maintaining appropriate levels of nutrients and waste products in the culture medium. Through these openings, culture medium can be removed and replaced without disturbing the membrane substrate.

U.S. Pat. No. 5,141,718 discloses an apparatus that combines a strip of insert wells with a plate containing tear shaped reservoirs. Each reservoir is comprised of a circular portion and a triangular portion. The strips are comprised of a plurality of tubular members attached to membranes. These strips are inserted into the plate such that each tubular member is immersed in a reservoir. The tubular member occupies substantially all of the circular portion of the reservoir. Access to the reservoir is accomplished through the triangular portion, without disturbing the membrane substrate. The problem with this insert strip plate apparatus is twofold. birst, the wells do not conform to the standard 96-well industry standard and thereby are not adaptable to much of the auxiliary equipment designed specifically for such plates. Second, the insert strips are comparatively unstable when measured against a plate that has its entire well structure permanently integrated into the plate itself.

The drug industry has for several years used inserts, such as shown in U.S. Pat. No. 5,026,649, for use in drug transport studies. Cells are grown to a confluent monolayer on a microporous membrane. Electrodes can be placed on either side of the membrane in order to test the confluency of the monolayer. Thereafter, a compound to be screened is added to the lower portion of the well, below the membrane. After a suitable incubation time, an assay of the solution on the other side, above the membrane, is performed. The presence and concentration of the compound on the other side of the membrane indicate- the compound's ability to transport through the particular cells comprising the monolayer. A need exists for a culture plate capable of performing these types of cell transport studies on an industrial scale for the screening of large numbers of drugs.

Industry standard microtest cluster plates are laid out with 96 wells, each having an approximate cross sectional area of 0.053 squre inches, in an 8×12 matrix (mutually perpendicular 8 and 12 well rows) with a spacing of 0.355 inches between the center lines of rows, both in the x and y directions. In addition, the height, length and width of the microtest 96-well plates are standardized. This standardization has resulted in the development of a large array of auxiliary equipment specifically developed for 96-well formats. The equipment includes devices that load and unload precise volumes of liquid in multiples of 8, 12, or 96 wells at a time. In addition, equipment is available to transmit light through individual wells and to read calorimetric changes or chemiluminescence in individual wells. Some of this equipment is automated and instrumented to record, analyze and manipulate the data recorded.

A problem associated with insert devices is that their size does not allow them to easily conform to the standard 96-well culture plate format. Insert devices suspend a membrane within a well. In order to suspend the membrane without it touching the walls of the well, the membrane itself must be substantially smaller in diameter than the diameter of the inside of the well. Further, access to the lower part of the well is accomplished by inserting a pipette or syringe to the side of the suspended membrane. Therefore, the suspended membrane must be not only small enough to prevent contact with the wall of the well, but also small enough to allow a pipette or syringe to fit between it and the well wall. In a 96 well plate, the diameter of the wells is relatively small (approximately 0.325 inches). Inserts that fit into these small wells have membranes that are considerably smaller in diameter than the wells. These small membranes are difficult to handle and perform studies upon.

The insert strips of U.S. Pat. No. 5,141,718 use more of the well space for the membrane because of an alternate access path to the lower part of the well. However, the membrane cannot occupy the entire cross sectional area of the well because the tubular inserts have walls which themselves occupy well space.

Another problem with inserts involves the means for accessing the lower chambers of wells. Inserts allow access to the lower portion of a well through openings in downwardly extending walls of the insert. While accessing the lower chamber, an unsteady hand may cause a pipette or syringe needle to hit the side of the opening and thus jar the entire insert, which may disturb the membrane substrate and cause damage to the cell later itself. Insert strips allow access to the lower chamber through an extension of a reservoir into which the strips are inserted. However, as with the well inserts, a pipette or syringe may disturb the membrane attached to the insert strip because access to the reservoir is immediately adjacent the insert.

The present invention solves both of these problems by supplying a plate with a membrane that covers the entire cross sectional area of a well of a standard 96-well format, while allowing access to the lower part of the well through distinctly separate access ports. The invention combines the industrial assay advantages of the standardized 96-well cluster plate with the functional advantages of cell culture inserts and insert strips.

SUMMARY OF INVENTION

It is therefore the object of the present invention to provide a multi-well cluster plate with which large scale drug transport studies can be performed. Another object is to provide a cluster plate having membranes suspended across the entire cross sectional area of the wells while providing access to the lower portions of those wells through adjacent access ports. A further object is to provide a cluster plate-type construction having the functional advantages of cell culture inserts but in a permanently integrated plate, thereby eliminating the need for well inserts. A further object is to provide an access port that is physically separate from the upper portion of a well, thereby significantly reducing the possibility of disturbing the cell growth substrate while accessing the lower chamber of the well. Another object is to provide a unique method of manufacture for the plates of the present invention.

Briefly, the present invention relates to an improved cluster plate and its method of manufacture. The cluster plate comprises a plurality of non-removable wells. The wells have an upper chamber and a lower chamber separated by a microporous membrane. Adjacent to each well is a corresponding access port. The access port is a separate opening in the top surface of the plate which provides direct access to the lower chamber of the corresponding well. The access port provides communication between the lower chamber and the ambient environment. The lower chamber of the well is of a greater cross sectional area than the combined cross sectional areas of the upper chamber and the access port.

The method of manufacturing the plate comprises several steps, namely: forming an upper plate having a plurality of upper chambers of predetermined diameter and a plurality of access ports of predetermined diameter, the upper chambers having side walls, and the access ports having side walls; forming a lower plate having a plurality of reservoirs, the cross-sectional area of each of the reservoirs being greater than the combined cross sectional areas of its corresponding upper chamber and access port, the reservoirs having a bottom wall; positioning a membrane between the upper plate and the lower plate, the membrane being either in the form of a sheet or individual discs fitted to the size of the upper chambers; bonding the upper and the lower plates together, so that respective upper chambers and access ports are aligned with each reservoir; and, if a sheet of membrane was used, the membrane material between the access ports and the reservoir is removed.

DESCRIPTION OF THE PREFERRED EMBODIMENTS

Figure 1:
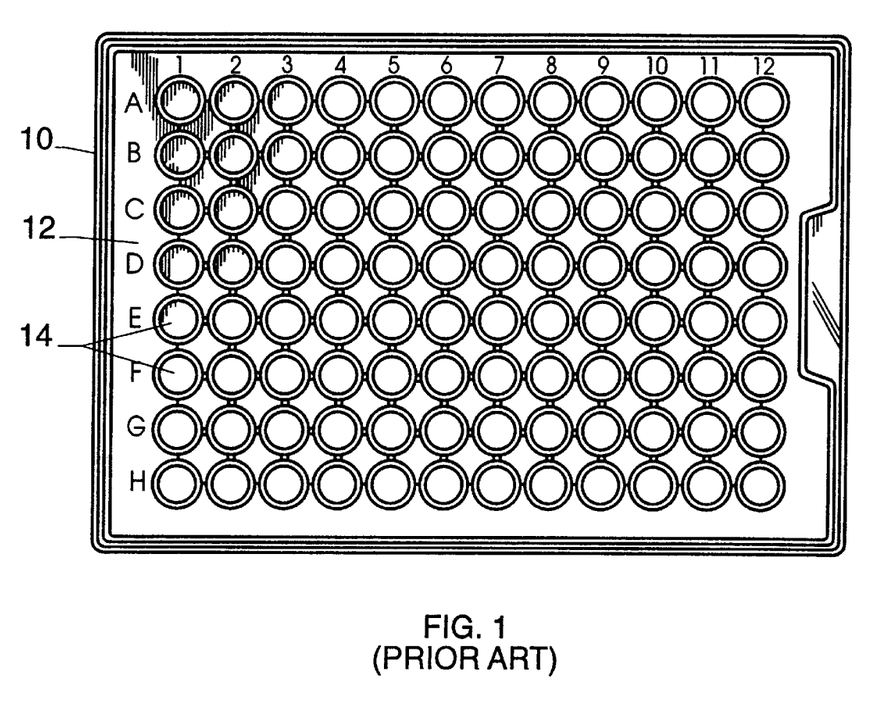
FIG. 1 is a plan view of a prior art 96-well cluster plate with its wells and overall dimensions conforming to the standardized format adopted by industry.
Figure 1A:
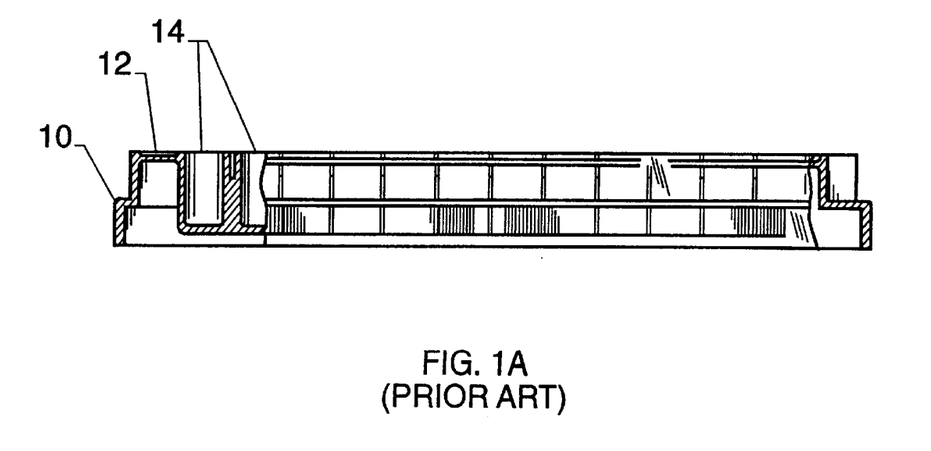

In FIG. 1, an example of a standard 96-well plate is shown. Its overall height, width, and length are standardized at 0.560, 3.365 and 5.030 inches, respectively. The plate includes a surrounding skirt 10, a top surface 12 and an array of wells arranged in 12 rows of eight wells each, to provide 96 identical wells in the plate. The top surface 12 extends between the skirt 10 and the periphery of the wells 14 on the outside of the 96-well matrix.

Industry standards prescribe that the center lines of the rows be spaced apart 0.355 inches, and similarly, the centers of adjacent wells in the same row be spaced apart the same distance. Each well on a standardized 96-well plate has a cross-sectional area of approximately 0.053 square inches. The cluster plates typically are molded of plastic and are provided with transparent covers (not shown) with drip rings to control water loss by evaporation, while allowing gas exchange and maintaining sterility.

As discussed above, the standardization of the format of the 96-well plate has led to the development of a substantial variety of equipment to perform liquid transfers to and from the wells, to transmit light through the wells, to read calorimetric changes or chemiluminescence in individual wells, and many other functions. The liquid transferring equipment is either hand or robotic operated, and much of the equipment used For analyzing the contents of wells is automated and instrumented to record, analyze and manipulate the data recorded. The present invention includes a multi-well cluster dish which is compatible with the auxiliary equipment designed for this format.

Figure 2:
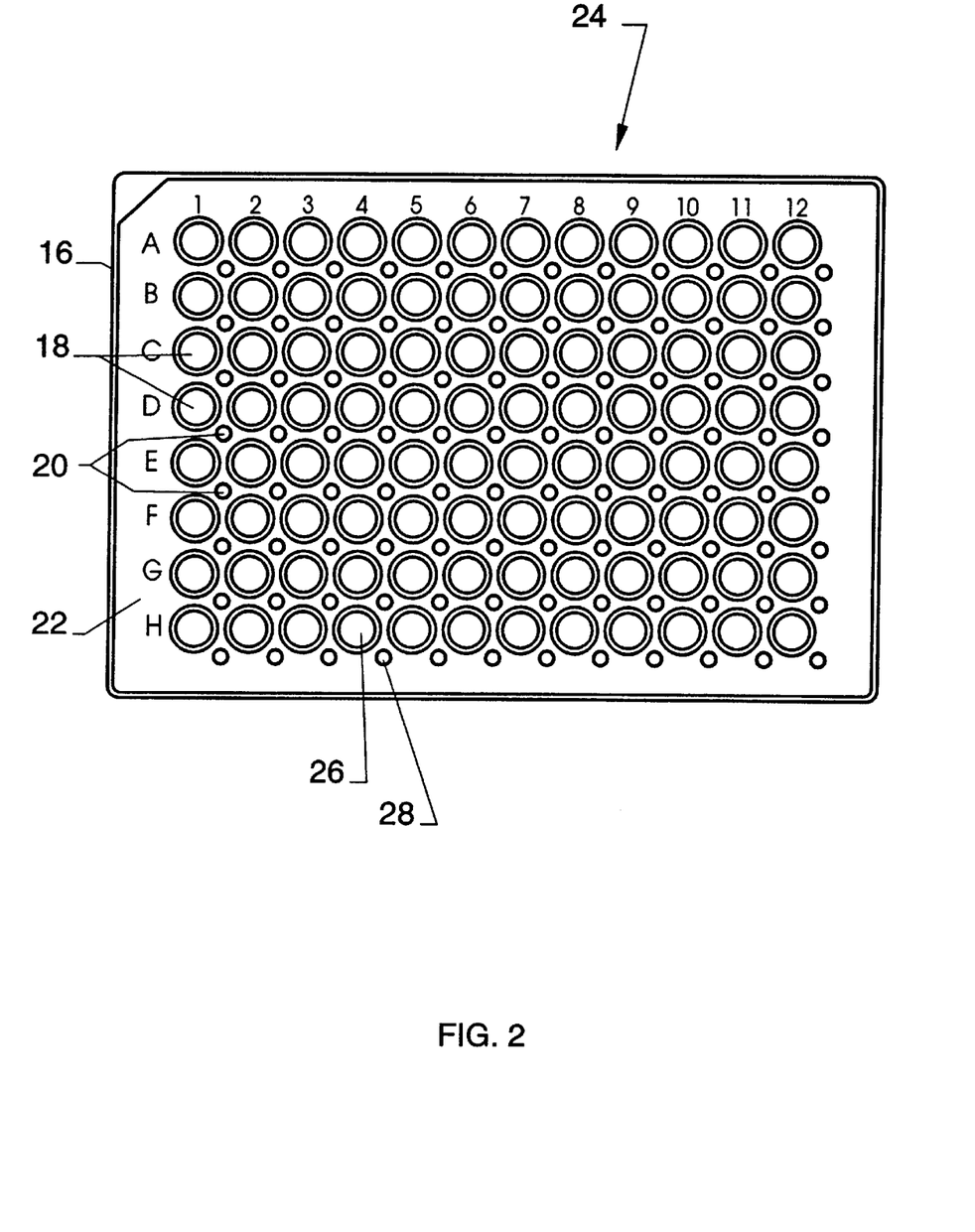
FIG. 2 is a plan view of an upper plate made in accordance with the present invention.

FIG. 2 shows an upper plate 24 which is preferably formed by injection molding and is preferably a pigmented opaque plastic (e.g. polystyrene or polypropylene). The upper plate includes a peripheral skirt 16 which ideally conforms to the dimensions of the skirt 12 of the standard 96-well plate, as well as, the overall length and width. The plate 24 has a top surface 22 and includes upper chambers 18 which are circular cylinders having side walls which are open at each end and extend through the plate 24 and are preferably arranged in 12 numbered rows spaced 0.355 inches apart, measured from the center line of one row to the center line of the next consecutive row. The rows preferably each contain 8 upper chambers preferably spaced 0.355 inches apart, on centers. Further, the center line of the first row is preferably disposed 0.565 inches from the skirt 16 on the left margin, as standardized by the industry.

Between each row of upper chambers and immediately following the last row of upper chambers, are rows of access ports 20. Access ports 20 are individual ports which also are circular cylinders having side walls which are open at each end and extend through the plate 24. The plate of FIG. 2 has one access port for each upper chamber. The rows of access ports are staggered from the rows of upper chambers, such that individual access ports 20 are located both between rows of upper chambers and between individual upper chambers 18 of each-h row. In the plate of FIG. 2, each upper chamber has a corresponding access port located below and to the right. As an example, referring to FIG. 2, upper chamber 26 corresponds with access port 28. The access ports 20 taken by themselves preferably also conform to the 96-well cluster matrix, i.e. are preferably arranged in 12 rows with port centers spaced 0.355 inches apart. The centers of consecutive individual access ports in each row are also preferably 0.355 inches apart. The center line of the first row of access ports, located between Row 1 and Row 2, is preferably disposed 0.740 inches from the skirt 16 on the left margin. This arrangement maximizes use of the space between wells.

Figure 3A:
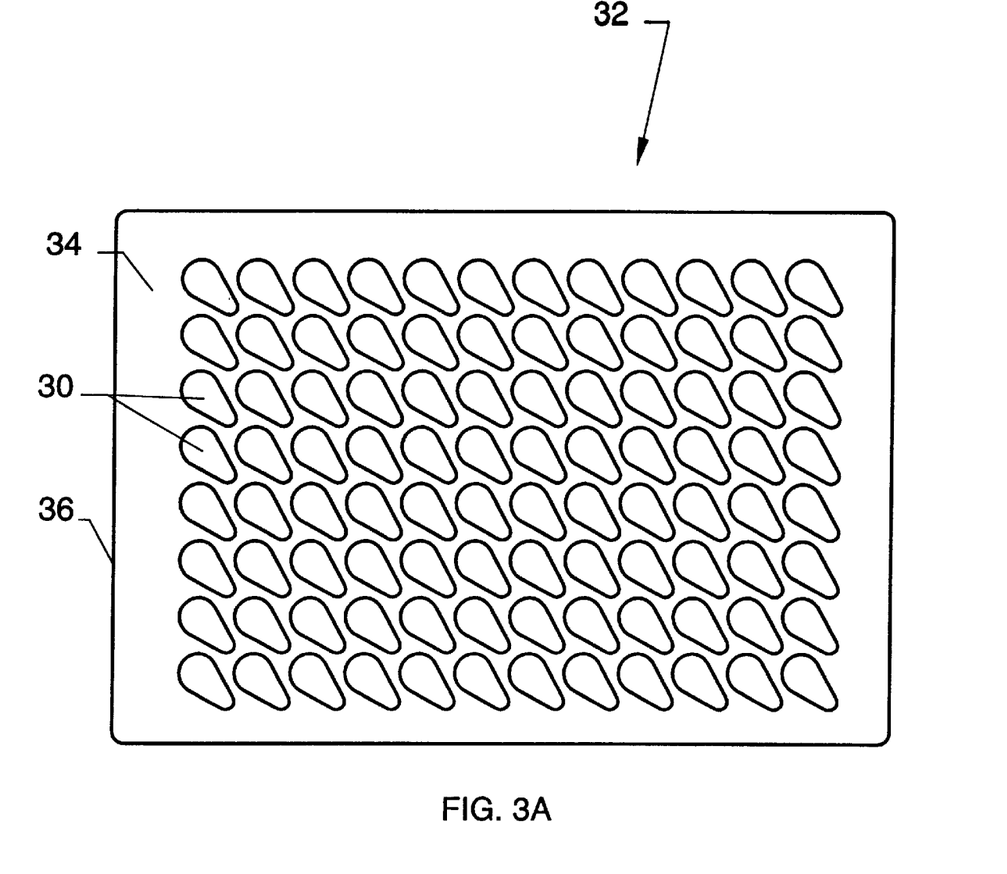
FIG. 3A is a plan view of a plate to be used as a lower portion and made in accordance with the present invention.
Figure 3B:
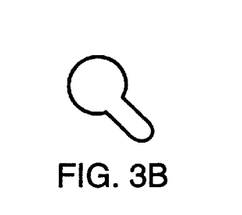
FIGS. 3B–3E are a plan views of separate embodiments for a shape design of a reservoir made in accordance with the current invention.
Figure 3C:
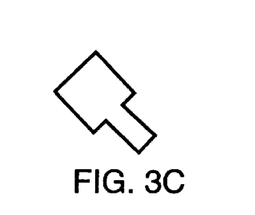
Figure 3D:
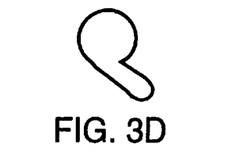
Figure 3E:
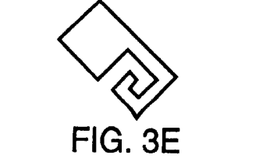
Figure 4:
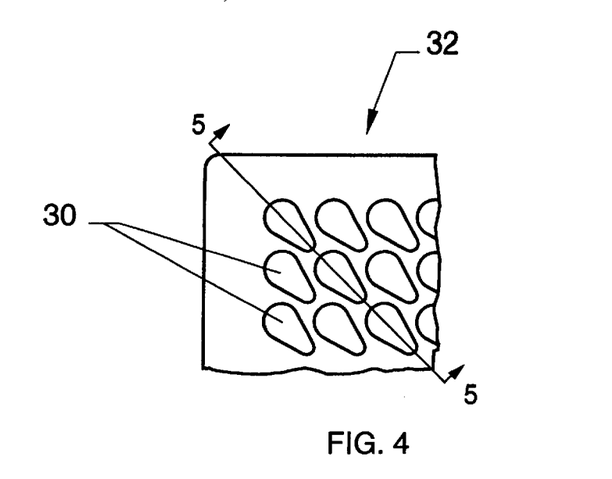
FIG. 4 is a closer view of a plate to be used as a lower portion of the present invention.

FIG. 3A shows a lower plate 32, which is preferably injection molded and is an optically clear plastic (e.g. polystyrene or polypropylene). The plate 32 includes a matrix of 96 tear shaped reservoirs 30 which are open at the top surface 34 and have a bottom wall. FIGS. 3A through 3E show alternate paddle shape designs for the reservoirs. "Paddle shape" shall mean any shape in which a relatively larger cross sectional area is connected to a smaller extension of lesser cross-sectional area. FIGS. 3B through 3E are examples of paddle shaped designs. FIG. 4 shows an enlarged corner section of the lower plate 32 of the present invention.

Figure 5A:
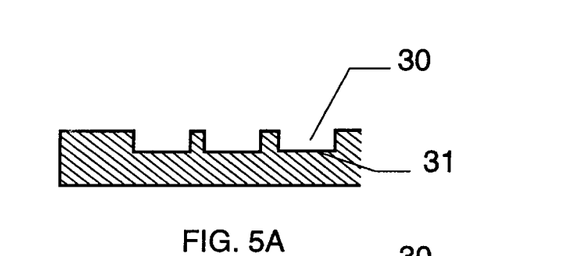
FIG. 5A is a fragmentary cross sectional view of one embodiment of the plate of FIG. 4, taken along the section line 5—5 in FIG. 4.
Figure 5B:
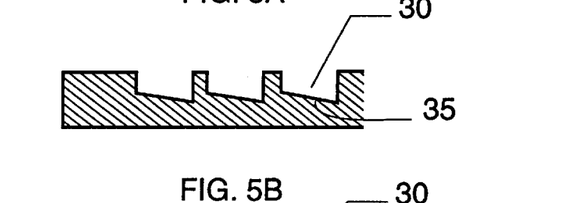
FIG. 5B is a fragmentary cross sectional view of one embodiment of the plate of FIG. 4, taken along the section line 5—5 in FIG. 4.
Figure 5C:
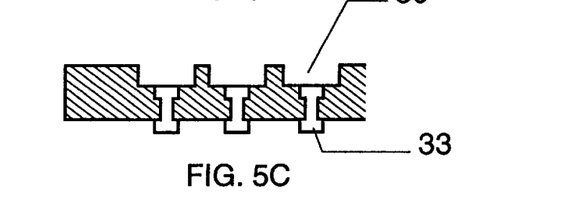
FIG. 5C is a fragmentary cross sectional view of one embodiment of the plate of FIG. 4, taken along the section line 5—5 in FIG. 4.
Figure 5D:
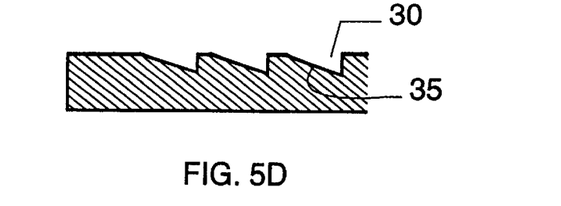
FIG. 5D is a fragmentary cross sectional view of one embodiment of the plate of FIG. 4, taken Long the section line 5—5 in FIG. 4.

FIGS. 5A through 5D show different embodiments for bottom walls of reservoirs 30. FIG. 5A shows a reservoir having a flat bottom wall 31. FIG. 5B shows a reservoir with a sloped or angled bottom wall 35. FIG. 5C shows a reservoir with an electrode 33 connecting the reservoir 30 with the bottom of the plate. FIG. 5D shows another reservoir with a slanted bottom wall 35.

Looking at FIGS. 2 and 3A together, each reservoir 30 in the lower plate 32 aligns with an upper chamber 18 and an access port 20 of the upper plate 24, such that when the upper plate 24 is positioned on the lower plate 32, each upper chamber 18 and access port 20 of the upper plate 24 communicates with a corresponding reservoir 30 of the lower plate 32.

The horizontal cross sectional area of the reservoir 30 is determined by the area enclosed by the circumference of the upper chamber 18, the circumference of the access port 20, and tangential lines connecting the circumference of the upper chamber to the circumference of the access port. In all cases, the cross sectional area of the reservoir is greater than the combined areas of the upper chamber and access port. For example, when compared to the cross sectional area of an upper chamber of a well that corresponds to a well of the standardized 96-well plate, the cross sectional area of the reservoir is greater than 0.053 square inches (the approximate cross sectional area of a well in the 96 well format). The center line of each reservoir is determined by imprinting the circumference of a respective upper chamber 18 from the upper plate 24 of FIG. 2 onto a respective reservoir 30, and connecting the centers of these circles. The reservoirs are arranged in 12 rows spaced 0.355 inches apart, measured from the center line of one row to the center line of the next consecutive row. The rows each contain 8 reservoirs. Reservoirs in each row are likewise spaced 0.355 inches apart, measuring from the reference center of one reservoir to the reference center of the next reservoir in the row. Further, the enter line of the first row is disposed 0.565 inches from left margin, in order to align with the upper plate 24. Additionally, any point along the periphery of any reservoir is spaced equidistantly (preferably 0.355 inches) from the same spot on the next corresponding reservoir, whether it is the next reservoir in the row, or the reservoir directly above or below it.

Figure 6:
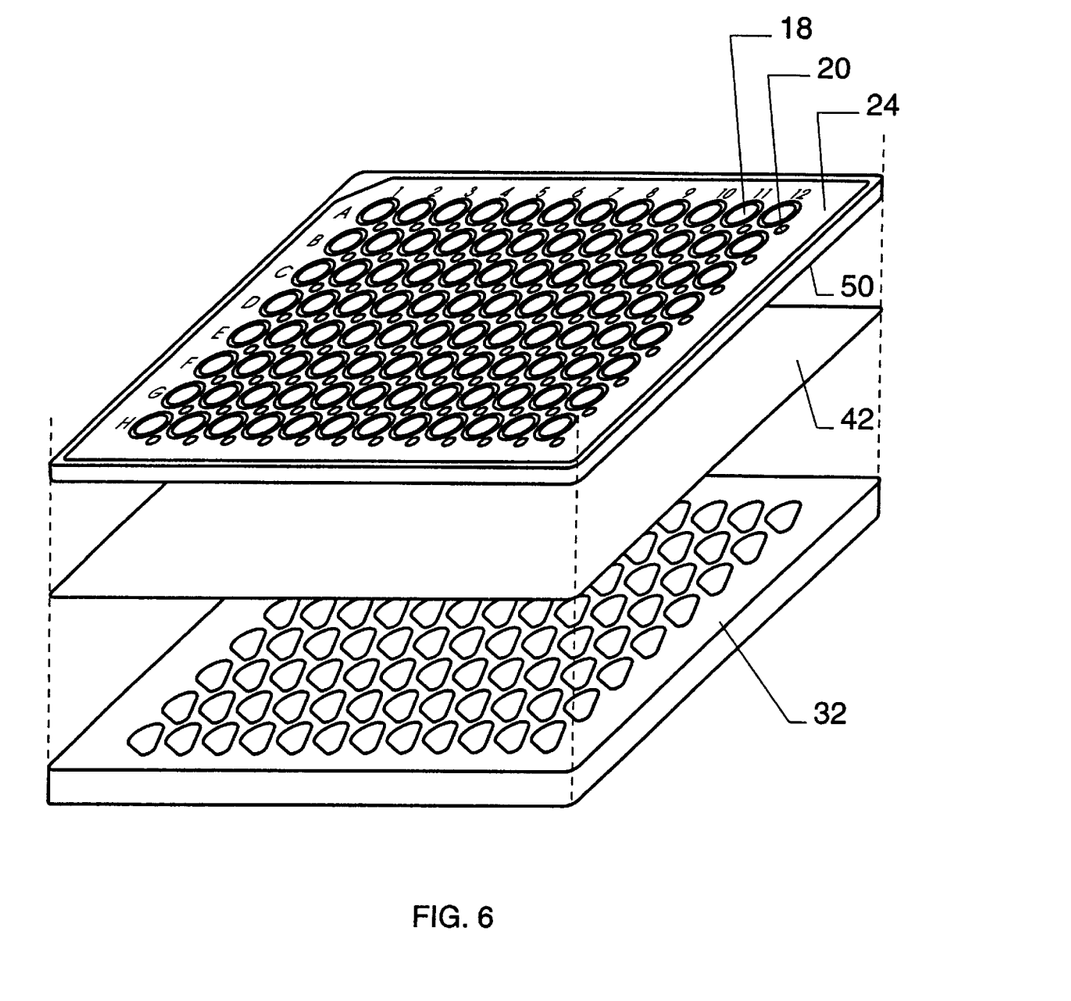
FIG. 6 is an exploded perspective view of a cluster plate of the present invention.

FIG. 6 shows an exploded view of the present invention. Placing a filter sheet between two plastic plates is known, as shown in U.S. Pat. No. 4,948,442. The preferred process of manufacturing the plate of the present invention involves several steps. First, a lower plate 32 is injection molded preferably with an optically clear plastic. The clear plastic will allow luminescent related assays to be performed from below the wells. Next, an upper plate 24 is injection molded, preferably with an opaque plastic. The opaque plastic will prevent optical cross-talk between the upper chambers 18 of the wells. Then, a membrane 42 sheet is positioned between the lower surface 50 of the upper plate 24 and the upper surface 34 of the lower plate 32, preferably by gluing using an adhesive sealant which is not toxic to cells. Alternatively, membrane discs may be attached individually to the bottoms of the upper chambers of the upper plate. Finally, the two plates are affixed together, preferably with adhesive, pressure sensitive film, or hot melt adhesive, such that an access port and an upper chamber of the upper plate align with each reservoir. If a membrane sheet was used in the process, the membrane material would be removed from the access ports, preferably by means of a vacuum punch. The height of the resulting cluster plate of the present invention preferably will be 0.560 inches, conforming to the 96-well plate industry standard.

Figure 7:
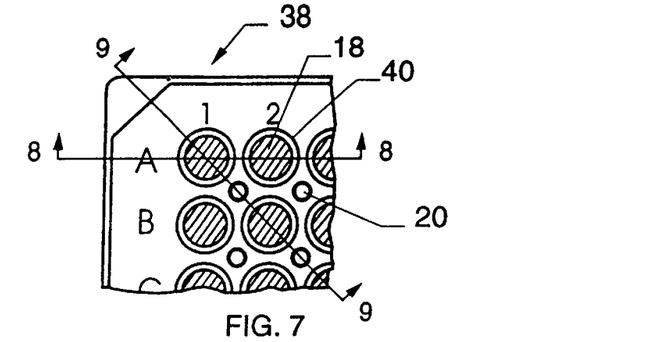
FIG. 7 is a view of the corner of a cluster plate made in accordance with the present invention.
Figure 8:
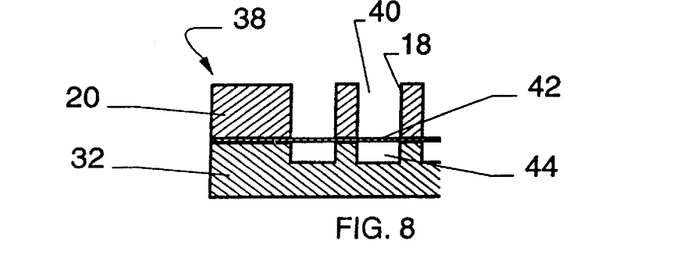
FIG. 8 is a fragmentary cross-sectional view of the cluster plate of FIG. 7, taken along the section line 8—8 in FIG. 7.
Figure 9A:
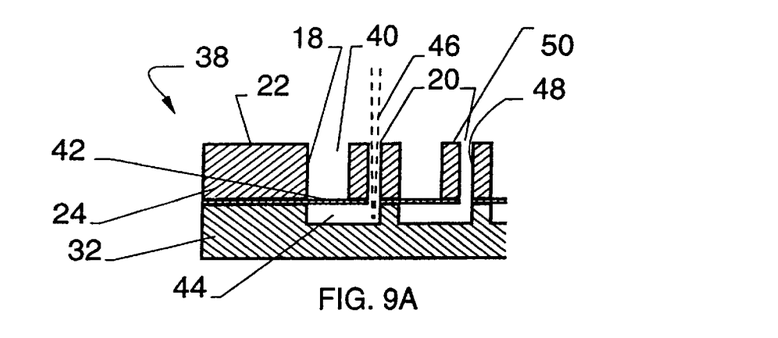
FIG. 9A is a fragmentary cross-sectional view of one embodiment of the cluster plate of FIG. 7, taken along the section line 9—9 in FIG. 7.
Figure 9B:
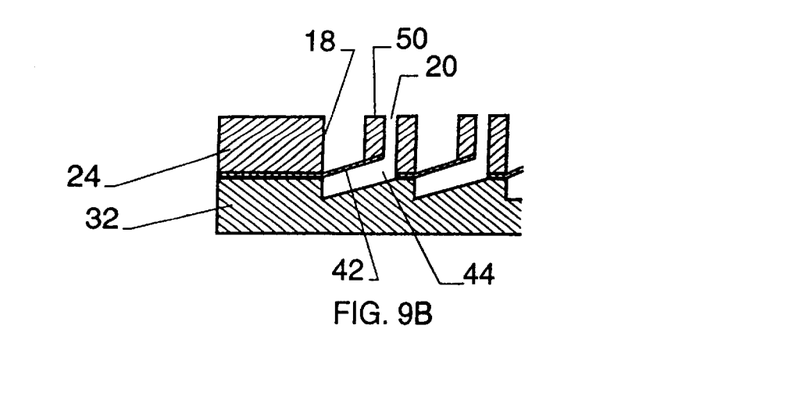
FIG. 9B is a fragmentary cross-sectional view of one embodiment of the cluster plate of FIG. 7, taken along the section line 9—9 in FIG. 7.

FIGS. 7–9 show the cluster plate 38 of the current invention. The larger circles represent the openings that extend into the upper chamber 18 of the well 40. The smaller circles represent access ports 20 that extend directly into a lower chamber 44 of the well 40. At the bottom of the upper chamber, and separating the upper chamber from the lower chamber of each well, is preferably a microporous membrane 42, for example as described in U.S. Pat. No. 5,376,273. The permeable membrane serves as a substrate for cell growth and is preferably track etched such as nucleopore (polycarbonate). Cast membranes of nylon, cellulose acetate or cellulose nitrate can also be used. The tear shaped reservoir 30 of FIG. 3A becomes the lower chamber 44 of a well 40 after the lower plate 32 is combined with the upper plate 24 and membrane substrate 42 to form the plate 38 of the present invention. As discussed, the reservoir, which becomes the lower chamber 44 of the well 40, may have a sloped bottom wall 35 (FIGS. 5B and 5D), or a flat bottom wall 31 (FIG. 5A). The slope in FIG. 5B serves to help funnel all the media to the side of the lower chamber 44 that aligns with the access port 20.

The membrane and surface of the upper chamber may be corona or plasma treated in order to obtain a hydrophilic surface. Alternatively or in addition, the lower chamber may be corona or plasma treated to create a hydrophillic surface and thereby reduce surface tension, which in turn aids in to preventing air entrapment.

For many biological studies, it is important to grow a confluent monolayer on the membrane substrate. In order to test the confluency of the cell monolayer, electrodes are placed on both sides of the membrane and an electrical potential is measured. The well design of the present invention allows for an electrode to be placed into the lower chamber, through the access port, with another electrode placed in the upper chamber of the well. The electrode to be placed in the lower chamber may be curved in such a way as to be positioned directly under the membrane surface. The electrical potential across the membrane surface can then be measured. Another embodiment shown in FIG. 5C has a lower electrode sealed within the lower plate. A conductive contact point permeates the bottom of each lower chamber. By placing another electrode in the upper chamber of a well, electrical potential across the membrane can then be measured.

FIG. 8 shows a fragmented cross section of two consecutive wells 40 of the present invention. The upper plate 24 and lower plate 32 are separated by a microporous membrane 42. The upper chamber 18 and lower chamber 44 are separated by the membrane which covers the entire junction between the upper chamber and the lower chamber.

FIG. 9A shows a fragmented cross section taken along the line 9—9 of FIG. 7 and through two wells 40 and their adjoining access ports 20. FIG. 9A illustrates the interrelationship between the wells and access ports. The upper chamber 18 of each well 40 is separated from the respective lower chamber 44 by a membrane 42. An access port 20 communicates directly with the lower chamber. The lower chamber can be reached by pipette or syringe needle 46 through the access port. It is through the access port 20 that media and drugs can be exchanged in the lower chamber 44 of the well, without disturbing the membrane substrate 42 that is positioned at the base of the upper chamber 18. The access port is distinctly separated from the upper chamber by side walls 48 and a section 50 of the top surface 22 of the cluster plate. This physical separation between the upper chamber and the access port reduces the chances of disturbing the membrane substrate. The upper plate 24 and lower plate 32 that make up the invention are separated by the microporous membrane 42. The upper plate can be divided into access ports 20 and upper chambers 18. The lower plate has a plurality of reservoirs 30 which become lower chambers 44 when the two plates are affixed to each other and the well components align.

FIG. 9B shows another embodiment of the current invention. The lower plate 32 and upper plate 24 are molded so as to provide a sloping contact area for the membrane 42 to attach. When attached, the membrane 42 slants upward toward the access port 20. This allows for gas from the lower chamber 44 to escape through the access port 20. The section of top surface 50 dividing the access port 20 and the upper chamber 18 is slanted at the end and has substantially less width than the rest of the upper plate 24. This embodiment requires that membrane discs be fitted onto the bottom of the upper chambers of the upper plate before the plates are affixed to one another.

Each individual well 40 can be divided into well components comprising an upper portion having an upper chamber 18 and an access port 20, a membrane substrate 42, and a lower chamber 44.

The multi-well plate of the current invention may have as few as one well having a corresponding access port, but preferably, one access port per well for all the wells on the plate.

Although a preferred embodiment of the invention has been disclosed, other embodiments may be perceived without departing from the scope of the invention, as defined by the appended claims.

What is claimed is:

1. A multi-well cluster plate comprising:

an upper plate having a plurality of upper chambers and access ports, each of said upper chambers being associated with an adjacent access port;

a membrane which forms the bottom of each of said upper chambers;

a lower plate having a plurality of tear or paddle shaped reservoirs, each reservoir having a bottom wall; and, said lower plate and said upper plate being affixed to one another so that each of said upper chambers and said associated access port is aligned with a corresponding reservoir.

2. The multi-well cluster plate of claim 1 wherein said upper plate further comprises a matrix of said upper chambers corresponding to a well matrix of a standard 96-well format.

3. The multi-well cluster plate of claim 2 wherein said lower plate further comprises a matrix of said reservoirs spaced to correspond to a well matrix of said standard 96-well format.

4. The multi-well cluster plate of claim 3 wherein the spacing between said access ports is the same as the spacing between wells in said standard 96-well format.

5. The multi-well cluster plate of claim 4 wherein said upper chamber has a predetermined diameter, said diameter being the same as a well diameter in said standard 96-well format.

6. The multi-well cluster plate of claim 1 wherein said bottom wall of said reservoir is slanted.

7. The multi-well cluster plate of claim 1 wherein said bottom wall of said lower chamber has an electrode integrated therein.

8. The multi-well cluster plate of claim 1 wherein said bottom wall of said reservoir is parallel with said top surface.

9. The multi-well cluster plate of claim 1 wherein said upper chamber and said access port are each capable of receiving an electrode.

10. The multi-well cluster plate of claim 1 wherein said upper chamber and said membrane are hydrophilic.

11. The multi-well cluster plate of claim 1 wherein said lower chamber is hydrophilic.

12. The multi-well cluster plate of claim 1 wherein said membrane is microporous.

13. The multi-well cluster plate as claimed in claim 12 wherein said membrane is track etched.

14. A multi-well cluster plate comprising:

a plate having a top surface and a plurality of well components;

said well components each having an upper portion and a lower chamber;

said upper portion having an upper chamber and an access port;

a membrane separating said upper chamber from said lower chamber;

said access port providing communication between said lower chamber and said top surface;

a section of said upper surface separating said access port from said upper chamber; and, said lower chamber having a bottom wall.

15. The multi-well cluster plate of claim 14 wherein said plate further comprises a matrix of said wells corresponding to a standard 96-well format.

16. The multi-well cluster plate of claim 15 wherein each of said wells has an access port.

17. The multi-well cluster plate of claim 16 wherein the spacing between said access ports is the same as the spacing between wells in said standard 96-well format.

18. The multi-well cluster plate of claim 17 wherein said upper chamber has a predetermined diameter, said diameter being the same as a well diameter in said standard format.

19. The multi-well cluster plate of claim 14 wherein said bottom wall of said lower chamber is slanted.

20. The multi-well cluster plate of claim 14 wherein said bottom wall of said lower chamber has an electrode intergrated therein.

21. The multi-well cluster plate of claim 14 wherein said bottom wall of said lower chamber is parallel to said top surface.

22. The multi-well cluster plate of claim 14 wherein said upper chamber and said access port are each capable of receiving an electrode.

23. The multi-well cluster plate of claim 14 wherein said upper chamber and said membrane are hydrophilic.

24. The multi-well cluster plate of claim 14 wherein said lower chamber is hydrophilic.

25. The multi-well cluster plate of claim 14 wherein said membrane is microporous.

26. The multi-well cluster plate of claim 22 wherein said membrane is track etched.

27. A multi-well cluster plate comprising:

a plate having a top surface and a plurality of non-removable wells;

said wells having an upper chamber and a lower chamber;

a membrane separating said upper chamber from said lower chamber;

said lower chamber having a bottom wall; and, at least one access port connecting said lower chamber with said top surface of said plate.

28. The multi-well cluster plate of claim 26 wherein said plate further comprises a matrix of said wells corresponding to a standard 96-well format.

29. The multi-well cluster plate of claim 27 wherein each of said wells has an access port.

30. The multi-well cluster plate of claim 28 wherein the spacing between said access ports is the same as the spacing between wells in said standard 96-well format.

31. The multi-well cluster plate of claim 29 wherein said upper chamber has a predetermined diameter, said diameter being the same as a well diameter in said standard 96-well format.

32. The multi-well cluster plate of claim 26 wherein said bottom wall of said lower chamber is slanted.

33. The multi-well cluster plate of claim 26 wherein said bottom wall of said lower chamber is parallel with said top surface.

34. The multi-well cluster plate of claim 26 wherein said upper chamber and said access port are each capable of receiving an electrode.

35. The multi-well cluster plate of claim 26 wherein said bottom wall of said lower chamber has an electrode intergrated therein.

36. The multi-well cluster plate of claim 26 wherein said upper chamber and said membrane are hydrophilic.

37. The multi-well cluster plate of claim 26 wherein said lower chamber is hydrophilic.

38. The multi-well cluster plate of claim 26 wherein said membrane is microporous.

39. The multi-well cluster plate of claim 37 wherein said membrane is track etched.

40. The plate of claim 39 wherein said bottom wall is slanted.

41. A plate for use as an upper portion of a multi-well cluster plate comprising:

a top surface having a plurality of upper chambers;

said chambers having walls extending downwardly from said top surface to a bottom;

said bottom capable of binding to a membrane;

said top surface having a plurality of access ports; and said access ports having walls extending downwardly from said top surface.

42. A process for manufacturing a multi-well cluster plate comprising the steps of:

a) forming an upper plate, said plate having a plurality of upper chambers of predetermined diameter and a plurality of access ports of predetermined diameter, each of which is smaller than the diameter of each of said upper chambers, each of said upper chambers having side walls, and said access ports having side walls;

b) forming a lower plate, said plate having a plurality of reservoirs, the horizontal cross-sectional area of each of said reservoirs being greater than the combined horizontal cross sectional areas of one of said upper chambers and one of said access ports, said reservoirs having a bottom wall;

c) positioning a membrane between said upper plate and said lower plate;

d) bonding said upper and said lower plates together so that an upper chamber and an access port are aligned with each said reservoir; and e) removing said membrane between each of said reservoirs and said access ports.

43. A process for manufacturing a multi-well cluster plate comprising the steps of:

a) forming an upper plate, said plate having a top surface defining a plurality of upper chambers of predetermined diameter and defining a plurality of access ports of predetermined diameter, said upper chambers having side walls, and said access ports having side walls;

b) forming a lower plate, said plate having an upper surface defining a plurality of reservoirs, the horizonal cross-sectional area of each of said reservoirs being greater than the combined horizontal cross sectional areas of one of said upper chambers and one of said access ports, said reservoirs having a bottom wall;

c) positioning at least one membrane disc between one of said upper chambers and one of said reservoirs; and d) bonding said upper and said lower plates together so that an upper chamber and an access pore are aligned with each said reservoir.

* * * * *